United States Patent [19]

Salimbeni et al.

[11] Patent Number: 5,571,807
[45] Date of Patent: Nov. 5, 1996

[54] 1,5 BENZOTHIAZEPINONE DERVATIVES THEIR PREPARATION AND PHARMACEUTICAL USE

[75] Inventors: Aldo Salimbeni; Saturnino Caliari; Francesco Fici; Elso Manghisi, all of Milan, Italy

[73] Assignee: Istituto Luso Farmaco d'Italia S.p.A., Milan, Italy

[21] Appl. No.: 397,904

[22] Filed: Mar. 31, 1995

Related U.S. Application Data

[63] Continuation of Ser. No. 941,127, filed as PCT/EP91/00742, Aug. 18, 1991, abandoned.

[30] Foreign Application Priority Data

Apr. 27, 1990 [IT] Italy ..................... 20160/90

[51] Int. Cl.$^6$ .................... A61K 31/55; C07D 417/06
[52] U.S. Cl. .......................... 514/211; 540/491
[58] Field of Search .................... 540/491; 514/211

[56] References Cited

U.S. PATENT DOCUMENTS 3,562,257  2/1971  Kugita et al. ................ 260/239.3
4,902,687  2/1990  Floyd et al. .................. 540/491

*Primary Examiner*—Robert T. Bond
*Attorney, Agent, or Firm*—Bucknam and Archer

[57] ABSTRACT

This invention relates to diltiazem analogs having the formula:

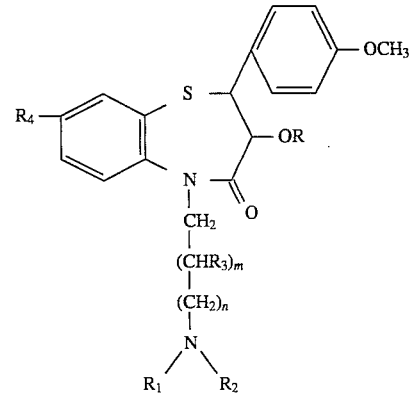

where the substituents are defined in the specification. These compounds are useful in treating cardiovascular problems. The invention also relates to a process for preparing the compounds and to pharmaceutical compositions containing the compounds.

3 Claims, No Drawings

1,5 BENZOTHIAZEPINONE DERVATIVES THEIR PREPARATION AND PHARMACEUTICAL USE

This is a continuation of application Ser. No. 07/941,127, filed Oct. 21, 1992, now abandoned.

The present invention relates diltiazem analogues, a process for their preparation and pharmaceutical compositions containing them.

Diltiazem, disclosed in U.S. Pat. No. 3,562,257, is a 1,5-benzothiazepinone derivative which, thanks to its calcium-antagonistic properties, is used in various cardiovascular pathologies such as hypertension and ischemic cardiopathy. The pharmacokinetics of diltiazem in humans is however characterized by a short elimination half-life whereby the drug must be administered every 4–6 hours, with problems of patient's compliance and with very non-constant plasma concentrations.

It has now been surprisingly found that 1,5-benzothiazepinone derivatives of general formula I, characterized by the presence on the basic nitrogen of at least a branched or cyclic alkyl group and/or by a substitution in the alkyl chain, are endowed with a longer duration of action in comparison with diltiazem, together with similar or higher calcium antagonistic properties.

The compounds of the invention have the following formula:

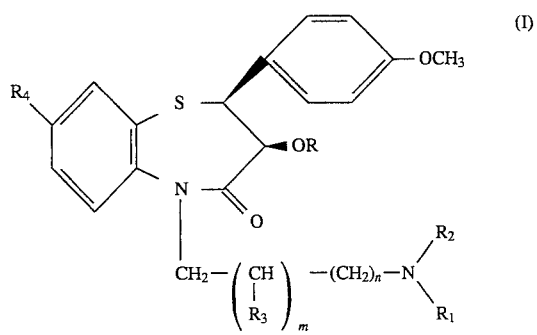

wherein R is hydrogen or an $R_5CO$ group wherein $R_5$ is a $C_1$–$C_4$ linear or branched alkyl or a phenyl group, optionally substituted by halogen atoms, methoxy or nitro groups; $R_1$ and $R_2$, which are the same or different, are a $C_1$–$C_4$ linear or branched alkyl or a $C_3$–$C_7$ cycloalkyl; $R_3$ is a $C_1$–$C_4$ linear or branched alkyl; $R_4$ is hydrogen, chlorine, methoxy; n is 1 or 2; m is zero or 1 with the proviso that when m is zero, at least one of $R_1$ and $R_2$ is a branched alkyl group or a cycloalkyl group.

The invention concerns also the diastereoisomers, the enantiomers or mixtures thereof of the compounds of formula I.

The groups in positions 2 and 3 are in cis position and their configuration is 2S, 3S.

U.S. Pat. No. 3,562,257 discloses compounds of formula I wherein m is zero and $R_1$ and $R_2$ are the same and represent lower alkyl groups. All the examples show compounds wherein $R_1$ and $R_2$ are methyl.

Other analogs of diltiazem are disclosed in GB 2143532, EP 256888 and WO 8912633.

This invention covers also the salts of the compounds I with pharmaceutically acceptable inorganic acids such as hydrochloric, hydrobromic, nitric, sulfunic, phosphoric acid and the like, as well as with pharmaceutically acceptable organic acids such as acetic, propionic, maleic, fumaric, malic, oxalic, tartaric, nitric, methanesulfonic acid and the like.

Particularly preferred compounds I are those wherein:

m is zero, n is 1, one of $R_1$ or $R_2$ is isopropyl, t-butyl, cyclopropyl, cyclohexyl and the other is methyl or isopropyl;

m is 1, n is 1, $R_3$ is methyl and $R_1$ and $R_2$ are as above defined;

m is 1, n is 1, $R_3$ is hydrogen and $R_1$ and $R_2$ are as above defined.

Particularly preferred compounds are those wherein $R_4$ is hydrogen and R is acetyl.

Examples of $C_3$–$C_7$ cycloalkyl residues are cyclopropyl, cyclopentyl, cyclohexyl.

The compounds of the inventions wherein R is hydrogen or a $R_5CO$ group wherein $R_5$ is as above defined, are prepared by reacting a benzothiazepinone derivative of formula II

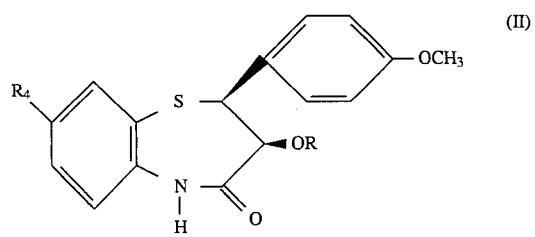

with a compound of formula III

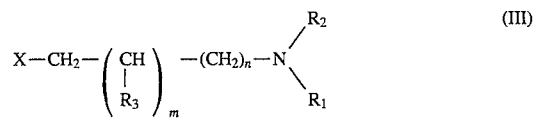

wherein m, n, $R_1$, $R_2$, $R_3$, $R_4$ are as above defined and X is halogen.

The so obtained compounds of formula I wherein R is H may be converted into the compounds I wherein R is $R_5CO$ by reaction with compounds of formula IV or their reactive derivatives $$R_5—COOH \qquad (IV)$$

wherein $R_5$ has the above defined meanings.

Alternatively, the compounds of formula I wherein R is a $R_5CO$ group wherein $R_5$ is as above defined, may be prepared by reacting a compound of formula V

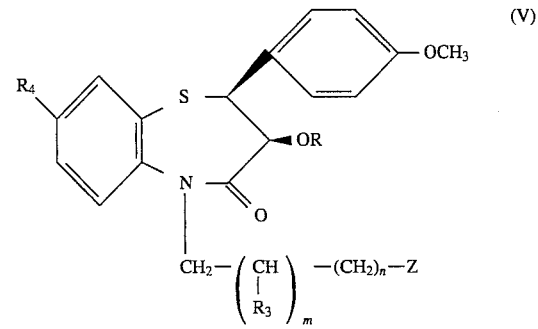

with an amine of formula VI

wherein m, n, $R_1$, $R_2$, $R_3$, $R_4$ are as above defined and Z is chlorine, bromine or a tosyloxy group.

The intermediates of formula V may be prepared from the corresponding compounds of formula II by reaction with the compounds of formula VII

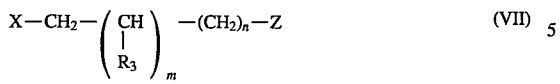

wherein X is chlorine, bromine and m, n, Z and $R_3$ have the above defined meanings.

The condensation of the compounds of formula II with a compound of formula III (optionally salified) is usually carried out in a solvent in the presence of an alkaline agent such as KOH, NaOH, $K_2CO_3$, NaH.

Examples of salts of formula III are hydrochloride, hydrobromide and the like.

The solvents may be selected from aliphatic ketones (acetone, methylethylketone etc), ethylacetate, dimethylsulfoxide, dimethylformamide, acetronitrile, tetrahydrofuran and dioxane.

The reaction is carried out at a temperature from 0° to 100° C., particularly from 20° to 70° C. The condensation of a compound of formula I wherein R is hydrogen with a compound of formula IV or with an active derivative thereof may be carried out in a solvent in the presence or in the absence of an acid acceptor. An active derivative of compounds IV may be an anhydride (e.g. acetic, propionic) or a chloride (acetyl chloride, propionyl chloride and the like). Pyridine, triethylamine, N-methylmorpholine and the like may be used as acid acceptors whereas suitable solvents are acetic acid, chloroform, methylene chloride, dimethylformamide, tetrahydrofuran. The reaction temperature ranges from 20° to 140° C.

The reaction for the preparation of compounds V may be carried out in an non-polar or polar solvent such as methanol, ethanol, dioxane, acetonitrile, tetrahydrofuran, N,N-dimethylformamide, methylene chloride, dimethylsulfoxide.

The reaction temperature ranges from 0° to 150° C. according to the boiling temperature of the solvent.

In order to neutralize the organic or inorganic acid HX released from the reaction, it is either possible to use an excess of the base VI or an inorganic base such as potassium or sodium carbonate.

Whenever the above reactions yield mixtures of diastereoisomers, these may be separated by usual methods (fractional crystallization, chromatography).

The compounds of formula I and their pharmaceutically acceptable salts have advantageous calcium antagonistic properties.

These properties were studied in vitro by displacement of 3H-diltiazem from its binding sites in the cardiac tissue (according to the method of H. Glossmann et al., FEBS 160, 226 (1983) or by the inhibition of the tonic contraction induced in the rabbit isolated atrium (according to the method of M. Spedding, Arch. Pharmacol. 318, 234 (1982)).

The p $IC_{50}$ and p $A_2$ values of several compounds of the invention are higher than 7. In vitro the compounds of formula I turned out to have remarkable and long-lasting anti-anginal properties as it was shown by the vasopressine-induced angina in the rat (according to the method of M. Leitold, H. Laufen, Arzneim, Forsch. 33, 1117 (1983)). Several compounds have $DE_{50}$'s comparable to that of diltiazem but with a longer duration. In pharmacokinetic studies carried out in the conscious incannulated rat, several compounds show an elimination t ½ after oral administration higher than that of diltiazem. The compounds I are also endowed with a favourable and long-lasting antihypertensive activity in the spontaneously hypertensive rat (SHR) test.

As an example, the biological properties of the compounds cis(+)-3-acetyloxy-2,3-dihydro-3-[2-(N-isopropyl-N-methylaminoethyl]-2-(4-methoxyphenyl)-1,5-benzothiazepin-4(5H)-one (Compound A) (Example 1) and of cis(+)-3-acetyloxy-2,3-dihydro-5-(2-methyl-3-dimethylaminopropyl)-2(4-methoxyphenyl)-1,5-benzothiazepin-4(5H)-one (Compound B) (diastereoisomer B, Example 3) in comparison with diltiazem.

|  | receptorial binding (pIC50) | rabbit isolated atrium (pA2) | angina vasopressine test rat (iv) ED50 | | pharmacokinetics in the rat (50 mg/kg/os) |
|---|---|---|---|---|---|
|  |  |  | duration |  |  |
|  |  |  | (mg/kg) | (min) | t ½ (min) |
| Compound A | 7.19 | 7.30 | 0.49 | 78 | 92 |
| Compound B | 7.52 | 7.20 | 0.54 | 72 | 71 |
| Diltiazem | 7.10 | 7.35 | 0.45 | 54 | 57 |

The compounds I or their pharmaceutically acceptable salts may be used in form of pharmaceutical compositions suitable for the oral or parenteral administration.

Usual excipients such as starch, lactose, glucose, arabic gum, stearic acid etc may be used. The pharmaceutical compositions may be in solid form such as tablets, pills, capsules or suppositories or in liquid forms such as solutions, suspensions or emulsions.

Moreover, if administered parenterally, the pharmaceutical preparations may be in form of sterile solutions.

The compounds I will be usually administered in unit doses ranging from 1 to 100 mg to patients affected by cardiovascular pathologies such as arrythmias, hypertension, ischemic cardiopathy.

The following examples further illustrate the invention.

The melting points are not correct, the identity of the compounds and their purity has been evaluated by elemental analysis (C,H,N) and IR, UV, NMR and mass spectrometry.

EXAMPLE 1

Cis(+)-3-acetyloxy-2,3-dihydro-5-(2-N-isopropyl-N-methylaminoethyl)-2-(4-methoxyphenyl)-1,5-benzothiazepin-4(5H)-one hydrobromide (a) A mixture of cis(+)-2,3-dihydro-3-hydroxy-2-(4-methoxyphenyl)-1,5-benzothiazepin-4(5H)-one (3.3 g), N-isopropyl-N-methylaminoethyl chloride hydrochloride (1.5 g) and $K_2CO_3$ (1.5 g) was suspended in 30 ml methyl ethyl ketone and refluxed for 12 hours. The residue was treated with ethyl ether and diluted with HCl (1:1). The organic phase was separated. The acid aqueous phase was made alkaline with 10% NaOH and extracted several times with ethyl ether. The organic phases were pooled and evaporated to dryness. The oily residue (3.1 g) was directly used for the subsequent reaction.

(b) The product obtained in (a) was dissolved in 31 ml acetic anhydride and let to stand for 12 hours. The acetic anhydride was distilled off under vacuum. The residue was dissolved in 32 ml ethyl ether and treated with a 6N HBr solution in isopropyl alcohol to acid pH. The precipitate was separated by filtration and crystallised from acetone-ethyl ether. 2.4 g white solid were obtained; m.p. 137°–140° C.

The following compounds were prepared according to the above procedure.

cis(+)-3-acetyloxy-5-(2-N-ethyl-N-methylaminoethyl)-2,3-dihydro-2-(4-methoxyphenyl)-1,5-benzothiazepin-4(5H)-one oxalate monohydrate; m.p. 105°–108° C. (ethyl acetate);

cis(+)-3-acetyloxy-5-(2-N-t-butyl-N-methylaminoethyl)-2,3-dihydro-2-(4-methoxyphenyl)-1,5-benzothiazepin-4(5H)-one oxalate; m.p. 86°–89° C. (isopropyl alcohol-ethyl ether);

cis(+)-3-acetyloxy-5-(2-N-cyclopropyl-N-methylaminoethyl)-2,3-dihydro-2-(4-methoxyphenyl)-1,5-benzothiazepin-4(5H)-one;

cis(+)-3-acetyloxy-5-(2-N-cyclohexyl-N-methylaminoethyl)-2,3-dihydro-2-(4-methoxyphenyl)-1,5-benzothiazepin-4(5H)-one;

cis(+)-3-acetyloxy-5-(2-N-diisopropyl-N-methylaminoethyl)-2,3-dihydro-2-(4-methoxyphenyl)-1,5-benzothiazepin-4(5H)-one oxalate; m.p. 86°–89° C. (isopropyl alcohol-ethyl-ether).

EXAMPLE 2

Cis(+)-3-acetyloxy-2,3-dihydro-5-(2-methyl-3-dimethylaminopropyl)-2-(4-methoxyphenyl)-1,5-benzothiazepin-4(5H)-one oxalate (diastereoisomer A)

(a) cis(+)-3-acetyloxy-5-(3-chloro-2-methylpropyl)-2,3-dihydro-2-(4-methoxyphenyl)-1,5-benzothiazepin-4(5H)-one.

5 g cis(+)-3-acetyloxy-2,3-dihydro-2-(4-methoxyphenyl)-1,5-benzothiazepin-4(5H)-one were dissolved in 30 ml dimethylformamide, cooled at −7° C. 1.4 g 88% KOH and, after 10 minutes, 3.8 g 1-bromo-3-chloro-2-methylpropane were slowly added. The temperature was then raised to 0° C. and the mixture was stirred for 4 hours. The reaction mixture was then poured in 250 ml 0.6N $NH_4Cl$ solution and extracted with $CH_2Cl_2$. The collected organic phases were washed with $H_2O$, dried on $Na_2SO_4$ and evaporated under reduced pressure. 6.4 g a thick orange oil were obtained and were dissolved in hot isopropyl alcohol. A crystalline solid precipitated by cooling, m.p. 100°–103° C.

The following compounds were prepared according the above procedure:

cis(+)-3-acetyloxy-5-(3-chloro-2-ethylpropyl)-2,3-dihydro-2-(4-methoxyphenyl)-1,5-benzothiazepin-4(5H)-one;

cis(+)-3-acetyloxy-5-(3-chloro-2-isopropyl)-2,3-dihydro-2-(4-methoxyphenyl)-1,5-benzothiazepin-4(5H)-one.

(b) 5 g chloro derivative, obtained as in (a), were dissolved in 30 ml dimethylformamide; 10 g dimethylamine and 0.05 g KI were added to the solution. The solution was then heated to 80° C. for 4 hours. The reaction mixture was then poured in 300 ml $H_2O$ and the separated solid was extracted with ethyl ether. The organic phase was evaporated to dryness and the residue was reacted with 35 ml acetic anhydride at room temperature. After 48 hours the excess acetic anhydride was eliminated and the residue was treated with ethyl ether. The white solid was separated and salified with oxalic acid in isopropyl alcohol. 3.5 g product, which were purified by isopropyl alcohol crystallization, were obtained; m.p. 177°–179° C. $[\alpha]_D^{20}=148$ ($H_2O$).

The following compounds were prepared according the above procedure:

cis(+)-3-acetyloxy-2,3-dihydro-5-[2-methyl-3-(N-cyclopropyl-N-methylamino)propyl]-2-(4-methoxyphenyl)-1,5-benzothiazepin-4(5H)-one;

cis(+)-3-acetyloxy-2,3-dihydro-5-[2-methyl-3-(N-cyclohexyl-N-methylamino)propyl]-2-(4-methoxyphenyl)-1,5-benzothiazepin-4(5H)-one;

cis(+)-3-acetyloxy-2,3-dihdyro-5-[2-methyl-3-(N-dimethylamino)propyl]-2-(4-methoxyphenyl)-1,5-benzothiazepin-4(5H)-one.

EXAMPLE 3

Cis(+)-3-acetyloxy-2,3-dihydro-5-(2-methyl-3-dimethylaminopropyl)-2-(4-methoxyphenyl)-1,5-benzothiazepin-4(5H)-one oxalate (diastereoisomer B)

5 g cis(+)-2,3-dihydro-3-hydroxy-2-(4-methoxyphenyl)-1,5-benzothiazepin-4(5H)-one, 2.9 g 2-methyl-3-dimethylaminopropylchloride hydrochloride, 5.7 g $K_2CO_3$, 1.4 ml $H_2O$ were reacted in 75 ml acetone, according to the procedure as in Example 1 (a), then reacted with 70 ml acetic anhydride, (see Example 1 (b)). The crude was treated with ethyl ether and the so obtained solid is filtered off and the solution was evaporated to dryness. This procedure was repeated. 4.3 g residue were dissolved in isopropyl alcohol and treated with 1.2 g oxalic acid. A solid, which was crystallized from acetone-ethyl ether, was obtained; m.p. 84°–89° C.; $[\alpha]_D^{20}=119.3$ ($H_2O$).

The following compounds were prepared according the above procedure.

cis(+)-3-acetyloxy-7-chloro-2,3-dihydro-5-(2-methyl-3-dimethylaminopropyl)-2-(4-methoxyphenyl)-1,5-benzothiazepin-4(5H)-one (starting from cis(+)-2,3-dihydro-7-chloro-3-hydroxy-2-(4-methoxyphenyl)-1,5-benzothiazepin-4(5H)-one).

EXAMPLE 4

Cis(+)-2,3-dihydro-5-(2-N-isopropyl-N-methylaminoethyl)-3-(2,2-dimethylpropanoyloxy)-2-(4-methoxyphenyl)-1,5-benzothiazepin-4(5H)-one and pharmaceutically acceptable salts thereof The raw material (obtained ad disclosed in Example 1 (a)), was dissolved in 15 ml anhydrous pyridine and treated with 0.23 g pivaloyl chloride. After 24 hours, the reaction mixture was poured in water and extracted with $CH_2Cl_2$. The organic phases were collected and evaporated to dryness. 0.9 g residue were converted to the corresponding maleic acid salt; m.p. 128°–130° C. (acetone-isopropyl ether).

We claim:

1. The compound cis(+)-3-acetyloxy-2,3-dihydro-5-(2-N-isopropyl-N-methylaminoethyl)-2-(4-methoxyphenyl)-1,5-benzothiazepin-4-(5H)-one, a diastereoisomer or enantiomer thereof and pharmaceutically acceptable salts thereof.

2. A method of treatment of a living subject affected by cardiovascular pathology which consists of administering to said living subject an effective amount of the compound cis(+)-3-acetyloxy-2,3-dihydro-5-(2-N-isopropyl-N-methylaminoethyl)-2-(4-methoxyphenyl)-1,5-benzothiazepin-4-(5H)-one a diastereoisomer or enantiomer or mixtures thereof or a pharmaceutically acceptable salt thereof.

3. The method according to claim 2 wherein said compound, said diastereoisomer or enantiomer or salt thereof or mixture thereof is administered in unit dose of 1–100 mgs.

* * * * *